United States Patent
Walden

(10) Patent No.: US 9,852,393 B2
(45) Date of Patent: Dec. 26, 2017

(54) CANNABIS CHAIN OF CUSTODY MANAGEMENT

(71) Applicant: Michael Walden, Dallas, TX (US)

(72) Inventor: Michael Walden, Dallas, TX (US)

( * ) Notice: Subject to any disclaimer, the term of this patent is extended or adjusted under 35 U.S.C. 154(b) by 0 days.

(21) Appl. No.: 14/663,373

(22) Filed: Mar. 19, 2015

(65) Prior Publication Data

US 2015/0278757 A1 Oct. 1, 2015

Related U.S. Application Data

(60) Provisional application No. 61/955,324, filed on Mar. 19, 2014.

(51) Int. Cl.
| | | |
|---|---|---|
| *G06F 7/00* | (2006.01) | |
| *G06Q 10/08* | (2012.01) | |
| *C07D 311/80* | (2006.01) | |

(52) U.S. Cl.
CPC ....... *G06Q 10/0838* (2013.01); *C07D 311/80* (2013.01)

(58) Field of Classification Search
CPC ............................ C12C 1/68; C12C 2563/185
USPC ........................................................ 235/376
See application file for complete search history.

(56) References Cited

U.S. PATENT DOCUMENTS

| | | | |
|---|---|---|---|
| 4,953,562 A | 9/1990 | Rosen et al. | |
| 7,378,675 B2 | 5/2008 | Ross et al. | |
| 7,488,954 B2 | 2/2009 | Ross et al. | |
| 7,682,797 B2 | 3/2010 | Thompson et al. | |
| 7,800,088 B2 | 9/2010 | Ross et al. | |
| 7,874,489 B2* | 1/2011 | Mercolino ........... | G01N 21/643 235/491 |
| 8,829,214 B2 | 9/2014 | Ismail et al. | |
| 9,095,554 B2 | 8/2015 | Lewis et al. | |
| 2005/0178058 A1* | 8/2005 | Rudolph .................. | A01G 9/16 47/60 |
| 2006/0037222 A1* | 2/2006 | Hunt ................ | G06K 19/06009 40/326 |
| 2006/0242899 A1 | 11/2006 | Parmenter | |

(Continued)

OTHER PUBLICATIONS

International Search Report and Written Opinion, PCT/US2015036844, dated Sep. 15, 2015.

(Continued)

*Primary Examiner* — Thien M Le
*Assistant Examiner* — Tae Kim
(74) *Attorney, Agent, or Firm* — Law Office of Sam Sokhansanj PLLC

(57) ABSTRACT

A method and system of managing a chain of custody for *cannabis* is provided that includes depositing one or more identification tags onto the surface of one or more *cannabis* seeds at a first custodian location, and depositing the identification tags onto the surface of one or more *cannabis*, wherein the *cannabis* plants are grown and matured from the *cannabis* seeds. The method and system further includes receiving the tagged *cannabis* plants at a second custodian location and extracting cannabinoids from the tagged *cannabis* plants, wherein the extracted cannabinoids include the one or more identification tags. In addition, the method and system further includes receiving the extracted cannabinoids at a third custodian location, wherein the extracted cannabinoids include the one or more identification tags which may be accumulated from all the prior custodians.

14 Claims, 4 Drawing Sheets

(56) References Cited

U.S. PATENT DOCUMENTS

| | | | |
|---|---|---|---|
| 2008/0082500 A1* | 4/2008 | Jung | G06F 19/363 |
| 2008/0102485 A1 | 5/2008 | Dodd | |
| 2012/0082997 A1 | 4/2012 | Keinan et al. | |
| 2012/0199651 A1* | 8/2012 | Glazer | G06Q 10/08 |
| | | | 235/376 |
| 2012/0311744 A1 | 12/2012 | Sirkowski | |
| 2013/0087144 A1 | 4/2013 | Todd | |
| 2014/0287068 A1 | 9/2014 | Lewis et al. | |
| 2014/0298511 A1* | 10/2014 | Lewis | A61K 36/185 |
| | | | 800/260 |
| 2014/0356858 A1* | 12/2014 | Harman | C12Q 1/68 |
| | | | 435/5 |

OTHER PUBLICATIONS

Crane, David, "Hitachi "Powder"/"Dust" μ-Chip Ultra-Small Micro RFID Chip with Embedded Antenna for Military and (Clandestine) Intelligence/Surveillance Applications: U.S. Military, Law Enforcement and Intelligence Agencies Licking their Chops?", Sep. 2012.

\* cited by examiner

CANNABIS CHAIN OF CUSTODY MANAGEMENT

CROSS-REFERENCE TO RELATED APPLICATION

This application claims the benefit of U.S. Provisional Application No. 61/955,324 filed on Mar. 19, 2014, which is incorporated herein by reference in its entirety.

BACKGROUND

This section is intended to introduce the reader to aspects of art that may be related to various aspects of the disclosure described herein and claimed below. This discussion is believed to be helpful in providing the reader with background information to facilitate a better understanding of the various aspects of the disclosure described herein. Accordingly, it should be understood that these statements are to be read in this light, and not as admissions of prior art.

Various techniques have been used for marking or tagging products in order to enable tracking the product or determining the source of a product under examination, such as the regulated *cannabis* or marijuana industry. For *cannabis* growers, harvesters, processors, distributors, and retailers, the current industry protocol is to physically attach or hang an identification tag, such as radio-frequency identification (RFID) labels, to the package of the *cannabis* seed, the stem or parts of a *cannabis* plant. In these known techniques, the tag is destroyed with product shipping or the transformation or conversion of the product into another form. Moreover, the tagging usually relates only to the source or identity of the respective product, and provides little or no information as to the history of the respective product. Further, during the chain of custody, the instance of counterfeiting, theft, or fraud increases wherein a human is in charge of physically attaching a tag and carrying over the same tag from a prior custodian or a new custodian, or creating a new tag for delivery to the new custodian. In addition, there are no means for clearly identifying where in a chain of custody the contents of a shipped marijuana product or package have been tampered with.

Hence, what is needed is an effective, low cost, and simple method of managing, identifying, and tracking of *cannabis* planting, growing, harvesting, processing and waste removal, packaging, distribution, retailing, and aftermarket product authentication by third parties, federal, and state regulatory agencies, among others.

BRIEF SUMMARY

One or more aspects of the disclosure described herein overcome the above shortfalls of prior attempted methods, devices, systems, and compositions. In particular, a *cannabis* chain of custody (CCC) management method, system, and composition is provided for effectively managing, identifying, tracking the chain of custody of *cannabis* from the seed to the final end user product, while being simple, low cost, reliable, and minimizing or eliminating human error, product theft, counterfeiting, while improving best practices procedures and compliance with audits, regulatory laws, agencies, and improving overall *cannabis* quality control, among other advantages further described within the disclosure herein.

In one aspect of the disclosure described herein, a method and system of managing a chain of custody for *cannabis* is provided that includes depositing one or more identification tags onto the surface of one or more *cannabis* seeds at a first custodian location, and depositing the identification tags onto the surface of one or more *cannabis*, wherein the *cannabis* plants are grown and matured from the *cannabis* seeds. The method and system further includes receiving the tagged *cannabis* plants at a second custodian location and extracting cannabinoids from the tagged *cannabis* plants, wherein the extracted cannabinoids include the one or more identification tags. In addition, the method and system further includes receiving the extracted cannabinoids at a third custodian location, wherein the extracted cannabinoids include the one or more identification tags which may be accumulated from all the prior custodians. Here, the first custodian location can include a seed grower or harvesting facility, the second custodian location can include a processing facility, the third custodian location can include a distribution and/or sub-manufacturer of food products for sale or further distribution to retailers or retail facilities.

The method and system can further include reading or detecting the identification tags at any of the first, second, or third, custodian locations. The method and system can also include transmitting the read or detected identification tags to a central database. Here, the reading or detection can be facilitated using one or more of the following methods including but not limited to photonic, magnetic, x-ray, radio frequency, chemical, microcode, florescence, genetic, electronic and spectroscopy analysis. In addition, the extraction can further include removing a binder that releases the one or more identification tags into the cannabinoid oil product, wherein the binder can only be removed through the extraction process and/or in combination with other solvents. Here, the identification tags can be mixed or dispersed within the cannabinoids as a suspension or colloid.

In another aspect of the disclosure described herein, a method and system of managing a chain of custody for *cannabis* is provided that includes depositing one or more identification tags onto the surface of one or more *cannabis* seeds at a first custodian location, and depositing the identification tags onto the surface of one or more *cannabis* plants at a second custodian location, wherein the *cannabis* plants are matured from the *cannabis* seeds. The method and system further includes receiving the tagged *cannabis* plants at a third custodian location and extracting cannabinoids from the tagged *cannabis* plants, wherein the extracted cannabinoids include the one or more identification tags. In addition, the method and system further includes receiving the extracted cannabinoids at a fourth custodian location, wherein the extracted cannabinoids include the one or more identification tags. Here, the first custodian location can include a seed grower facility, the second custodian location can include a plant harvesting facility, the third custodian location can include a processing facility, and the fourth custodian location can include a distribution or retail facility.

In another aspect of the disclosure described herein, a method and system for managing a chain of custody for *cannabis* is provided. The method and system can include receiving at a central repository taggant data of a *cannabis* batch from a first, second, and third custodian, and confirming the identification of the *cannabis* batch from the received taggant data, wherein the confirmation is comprised of determining that the received taggant data from the second custodian at least partially matches the first custodian taggants data, and wherein the taggant data of the third custodian at least partially matches the taggant data of either the first or second custodian or the combined taggant data of the first and second custodian. Here, the second custodian may include processing or extraction facilities, the third custodian may include distribution facilities. Further, the central repository can be operated by federal, state, city, or government agencies.

The above summary is not intended to describe each and every disclosed embodiment or every implementation of the disclosure. The Description that follows more particularly exemplifies the various illustrative embodiments.

BRIEF DESCRIPTION OF THE DRAWINGS

The following description should be read with reference to the drawings, in which like elements in different drawings are numbered in like fashion. The drawings, which are not necessarily to scale, depict selected embodiments and are not intended to limit the scope of the disclosure. The disclosure may be more completely understood in consideration of the following detailed description of various embodiments in connection with the accompanying drawings, in which.

DETAILED DESCRIPTION

Figure 1:
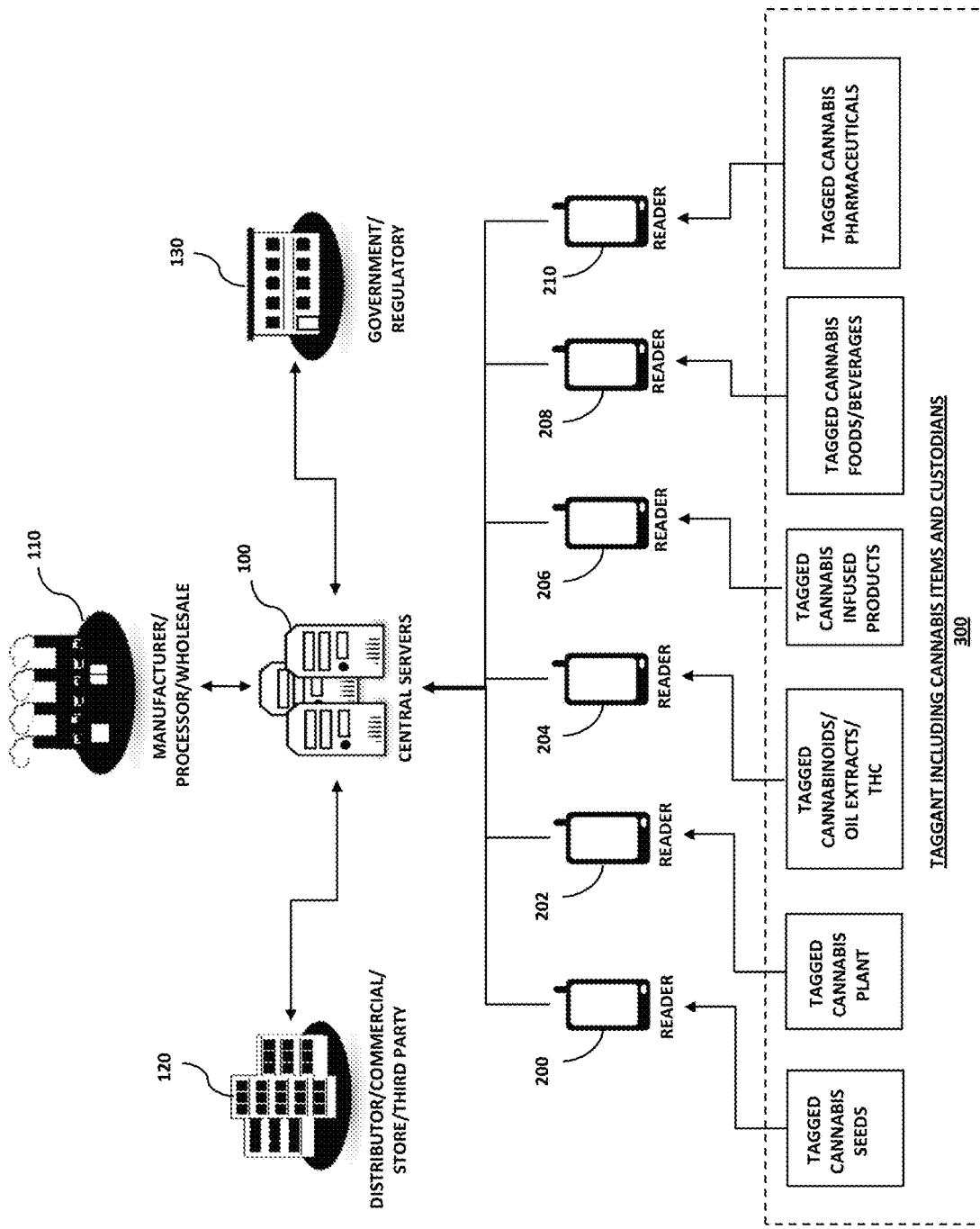
FIG. 1 illustrates network architecture for one non-limiting embodiment of the *cannabis* chain of custody (CCC) system of the disclosure described herein.

In the Brief Summary of the present disclosure above and in the Detailed Description and the claims below, and in the accompanying drawings, reference is made to particular features (including method steps) of the disclosure described herein. It is to be understood that the disclosure of the disclosure described herein in this specification includes all possible combinations of such particular features. For example, where a particular feature is disclosed in the context of a particular aspect or embodiment of the disclosure described herein, or a particular claim, that feature can also be used, to the extent possible, in combination with and/or in the context of other particular aspects and embodiments of the disclosure described herein, and generally in the disclosure described herein.

Phrases and terms similar to "*cannabis*", "cannabinoids", "end product", or "oil" may also be characterized as or may include but is not limited to marijuana, hemp, weed, hashish, hashish oil, *cannabis sativa, cannabis indica,* or *cannabis ruderallis, cannabis* oils, psychoactive ingredients/compositions, phytocannabinoids, synthetic cannabinoids, phytocannabinoid tetrahydrocannabinol (THC), cannabidiol (CBD), aminoalkylindoles, 1,5-diarylpyrazoles, quinolines, and arylsulfonamides, as well as eicosanoids related to the endocannabinoids, and other *cannabis* derived compounds, drugs, compositions, or ingredients, either in living/non-living, solid, liquid, or vapor form.

More specifically, cannabinoids are a class of diverse chemical compounds that act on cannabinoid receptors on cells that repress neurotransmitter release in the brain. Ligands for these receptor proteins include the endocannabi-noids (produced naturally in the body by humans and animals), the phytocannabinoids (found in *cannabis* and some other plants), and synthetic cannabinoids (manufactured artificially). The most notable cannabinoid is the phytocannabinoid tetrahydrocannabinol (THC), which is the primary psychoactive compound of *cannabis*. Cannabidiol (CBD) is another major constituent of the plant. As for separation from a *cannabis* plant, cannabinoids can be separated by extraction with organic solvents or other means known in the art. Hydrocarbons and alcohols are often used as solvents. However, these solvents are flammable and many are toxic. Further, butane may be used, which evaporates extremely quickly. Supercritical solvent extraction with carbon dioxide is an alternative method which can be used. Using the supercritical solvent extraction method, solvent removal is simple and efficient, and extract quality can be well controlled. Once extracted, cannabinoid blends can be separated into individual components using wiped film vacuum distillation or other distillation techniques. In addition, to produce high-purity cannabinoids, chemical synthesis or semisynthesis can also be used.

Phrases and terms similar to "tags" or "taggant" may include any type of identification code, indicia, particles, micro-particles or nano-particles, that can be based on visual colors, fluorescent compounds, phosphorescent compounds, infrared compounds, near-infrared, upconverting phosphors, semiochemical-mediated nano-taggants, etc. A possible composition of such taggants may include but is not limited to encapsulate DNA in heat-resistant and inert magnetic particles and with magnetic separation and particle dissolution, the DNA may be recovered unharmed and analyzed by quantitative real-time PCR and Sanger sequencing, biodegradable compositions, polysaccharides, starches, polypeptides, proteins, poly-amides, polyglycols, fatty acids, polyester, triglycerides, etc. Specific material compositions may also include poly-lysine and poly-aspartic acid based polymers. Further taggant or coding systems may also include a two-dimensional barcode system in which the barcode is placed into or onto a particle. Codes can be stamped, embossed, or laser etched on the taggant particles. The taggants may include multiple signals and encoded codes that can be detected and/or decoded. The signals or encoded codes can be detected individually or together, such as serially or in parallel. Suitable signals may include the presence or absence of detectable (e.g., visible or ultraviolet dye) markers, presence or absence of magnetic separation systems (e.g., magnetic or magnetically-attractable particles). Further, metals such as titanium, gold, silver, zinc, magnesium, iron, or metal compounds such as carbides or nitrides, for example, TiN, TiC, TiOxCyNz, may also be in the taggants to improve visibility and add coloration, and add overt recognition without compromising edibility. All of the aforementioned systems can be used singly or in combination and kits provided with directions for any specific marker or combination of markers. The taggants can also include carriers and binders, wherein the binders can be soluble or dissolvable during the extraction process of the *cannabis* plant. In addition, the taggant particles are non-toxic to animals, humans, and the environment and are generally regarded as safe (GRAS) substances approved by the FDA and can be used to satisfy this requirement of being non-toxic to humans and can be incorporated into food inputs and foodstuffs.

Phrases and terms similar to "software", "application", and "firmware" may include any non-transitory computer readable medium storing thereon a program, which when executed by a computer, causes the computer to perform a method or function.

Phrases and terms similar to "network" may include one or more data links that enable the transport of electronic data between computer systems and/or modules. When information is transferred or provided over a network or another communications connection (either hardwired, wireless, or a combination of hardwired or wireless) to a computer, server, repository, or database, wherein the computer uses that connection as a computer-readable medium. Thus, by way of example, and not limitation, computer-readable media can also comprise a network or data links which can be used to carry or store desired program code means in the form of computer-executable instructions or data structures and which can be accessed by a general purpose or special purpose computer.

Any discussion of a reader, scanner, tag reader, taggant reader, taggant detector, mobile device, computing device, or end device may also apply to any type of electronic networked device, including but not limited to phones such as cellular phones (e.g., an iPhone®, Android®, Blackberry®, or any 'smart phone'), a personal computer, tablet computer, wearable watch, Android® device, iPad®, Google® Glasses, server computer, laptop computer, personal digital assistants, x-rays, microscopes, spectroscopy devices and instruments, marker readers, RFID readers, magnetic reading instruments/devices, image analysis devices, photoelectric analysis, photonic instruments/devices, wave/light analysis, chemical reader/analysis/instrument devices, and roaming device, such as a network-connected roaming device, a wireless device such as a wireless email device or other device capable of communicating wireless with a computer network or server, or any other type of network device that may communicate over a network and handle electronic transactions. Any discussion of any mobile device mentioned may also apply to other devices.

FIG. 1 illustrates one embodiment for general network system architecture of the chain of custody (CCC) management system. Here, the CCC system can include one or more central databases, repositories, or servers 100 in bi-directional communication over a network with one or more of government or regulatory agencies 130; manufacturer, grower, harvester, processor, wholesaler 110; distributor, commercial entity, merchant, third party 120. Here, each of parties 110, 120, and 130 may be one or more of servers, databases, networks, computing devices, among others. Further, it is contemplated within the scope of the disclosure described herein that there may be any number of other entities that may communicate with central server 100. In addition, tag/taggant/identification readers 200, 202, 204, 206, 208, and 210 can also communicate bi-directionally with central server 100. Here, readers 200-210 operate to detect, read, decode, sense, or scan identification, tag, taggant, code, encoded data from one or more of tagged *cannabis* items or products 300, which will later be described in detail within this disclosure. The readers 200-210 can transmit the tagged data to the central server 100 and/or to one or more of entities 110, 120, and 130. In addition, any of entities 110, 120, 130, or server 100 may control or manage taggant readers 200-210, such as requesting detected identification tags data from the *cannabis* products 300 prior to, during, or after receipt of the *cannabis* at a custodian location. Here, readers 200-210 may also transmit taggant data automatically to server 100 or any one of entities 110, 120, and 130. It is contemplated within the scope of the disclosure described herein that any other configuration or network architecture, computing devices, and modules may also be incorporated. In one embodiment, the taggant data can include metadata or other data that can be linked to more in-depth data as the central server.

Figure 2:
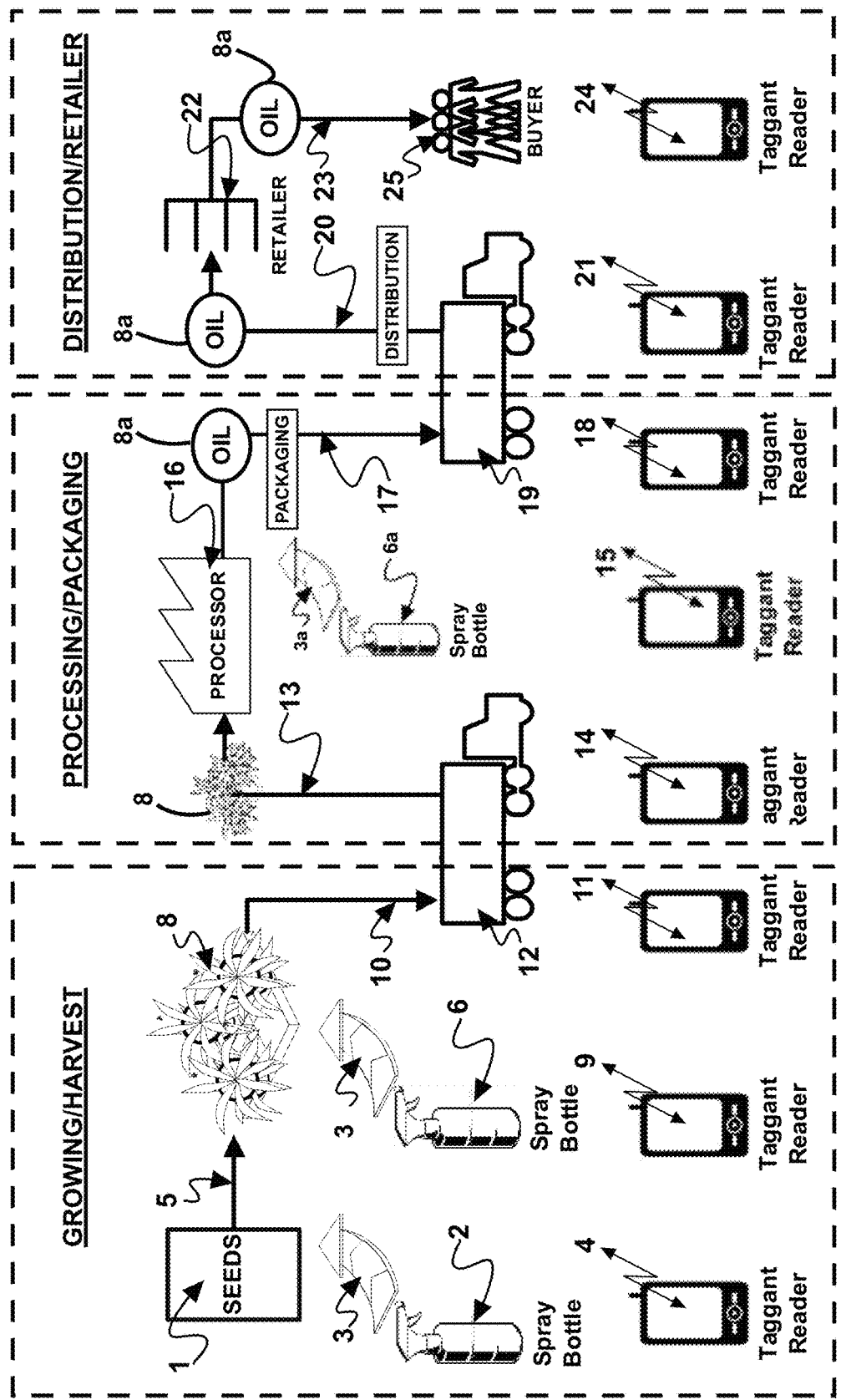
FIG. 2 illustrates a general overview diagram for one non-limiting embodiment of the *cannabis* chain of custody (CCC) method and system of the disclosure described herein.

FIG. 2 illustrates one general overview diagram for one embodiment of the *cannabis* chain of custody (CCC) management device, system, and method of the disclosure described herein. More specifically, the CCC system is not limited to *cannabis* or marijuana and can also be applicable to the chain of custody tracking, management, and identification of all types of agricultural, plant, medicinal, food, drug, or pharmaceutical materials and end products. Here, the CCC system can include one or more *cannabis* taggants and extraction systems. Here, taggants can include but are not limited to physical, molecular, chemical or biological. Extraction system or extraction equipment can incorporate or include supercritical $CO_2$ fluid extraction systems and methods.

Referring to FIG. 2, a specific coded or encoded taggants 3 in a tank or bottle 2 can be sprayed, bombarded, or deposited onto one or more seeds 1 that may be within a package, container, or vessel, wherein the taggants adhere, bond, or bind with the seeds. Alternatively, the seeds 1 may be placed, dipped, or soaked inside of a container, chamber, or vessel having the taggants, wherein the taggants adhere, bond, or bind to the seeds. Taggant reader 4 can be used to confirm the taggant code that is sprayed or deposited on seeds 1. The taggant reader may be any type of reader suitable to read the specific taggants. For example, the taggant reader may be a wireless device which may read, decode, scan and/or send the results or output to a central computer, database, or server or locally store the data in the taggant reader memory for access at a later time. The tagged seeds 1 are delivered 5 to a growing area that can grow or sprout the seeds 1 to a grown or matured plant 8, wherein the growing area may be a green house, field or other suitable medium. Here, in one embodiment, the matured plants can be used to create new plants by using cuttings to sprout instead of growing from the seeds. Here, these cuttings, which can be about eight inches in length, can be treated with a root promoter and placed in soil. In addition, these cuttings will also have taggants sprayed or deposited on them. Once the *cannabis* or plant grower has determined that the seeds 1 have acceptably grown to plant 8, then prior to harvesting, the plant 8 and its buds can be sprayed a second time or one or more iterations with the same taggants 3 or a different taggants using bottle 6 or bottle 2, wherein the taggants adhere, affix, bond, or bind to the plant. It is contemplated within the scope of the disclosure described herein that the taggants can also be deposited on the plants, or the plants can be dipped or placed in a container, chamber, or vessel having the taggants, wherein the taggants adhere, affix, bond, or bind to the plant. Next, the grown/growing medium or plant 8 can be segregated or separated into manageable growth batch areas, and each batch area further checked and identified for taggants 3 with the same taggants reader 4 or taggant reader 9 in order to further record, track, identify, and manage the *cannabis* chain of custody and inventory. In one embodiment, the spraying of plants 8 can ideally be divided into unique tag codes for each of the batches, wherein each batch may then accommodate the size of the shipping packages or other means of delivery.

Still referring to FIG. 2, after the plants 8 have grown to the desired size, they can be harvested and delivered 10 to a transport truck or vehicle 12. Prior to delivery to transportation, the harvested plants 8 can be further checked and identified by the same taggants readers 4, 9, or with a different reader 11 for taggants 3 in order to further record, track, identify, and manage the *cannabis* chain of custody and inventory. Once the one or more batches of plants 8 are delivered, the transport or delivery vehicle can be unloaded and the plants delivered 13 to a *cannabis* or plant processor or extraction facility 16. Prior to delivery 13 or after delivery 13 to processor 16, the batches or plants 8 can be checked again by a taggant reader 14 in order to further record, track, identify, and manage the *cannabis* chain of custody and inventory. It is contemplated within the scope of the disclosure described herein that there may be a plurality or sets of unique taggant codes representing separate plants 8 or grown plant batches delivered by the transport vehicle.

Still referring to FIG. 2, at the processor or extraction facility 16, the plants can be processed and extracted using a variety of extraction equipment, systems, or methods, such as a supercritical CO2 fluid extraction system shown in FIG. 4, which will be explained later in this document. It is contemplated within the scope of the disclosure described herein that there may be one or more pre-processing processes or steps taken before using the extraction equipment. Prior to, during, or after the processing or extraction of *cannabis* plants 8, the processed output *cannabis* product or extracted medium or oils can be checked again for taggants code 3 using a taggant reader 15. Here, it is noted that the taggants on the matured plants 8 that were grown from the original tagged *cannabis* seeds will pass through the processors extraction equipment FIG. 4, and be available to confirm their unique taggant code, such as taggant code 3. More specifically, the taggants or taggants 3 being applied on the surface of the plants are also present in the extraction equipment oil final product. When the processing is complete, each batch or final *cannabis* product, *cannabis*/THC oils, or cannabinoids 8a can be decanted, bottled, packaged and prepared for delivered 17. Here, prior to, during, or after delivery 17, the final product or cannabinoids 8a can be checked, read, and confirmed to have taggants 3 with using a taggant reader 18, in order to further record, track, identify, and manage the *cannabis* chain of custody and inventory. Once the taggants have been checked, the final product 8a can be loaded on to a transportation or delivery vehicle 19 for delivery to the next destination, such as further processing, distilling, quality control, packaging, cooking, retail, or wholesale destination or facility. For example, cannabinoids 8a can be in liquid, solid, or vapor form and also be incorporated in smoking form or items, vaporizable items, injectable items, and food, nutritional, or edible items or products. More specifically, the final product 8a may be intravenous, inhalable, topical, transdermal, transmucosal, intramuscular, epidural, intracereberal, and/or subcutaneous, among others. In addition, the final composition or product 8a can be provided and/or administered in powder, chunks, blocks, seeds, granules, drops, injectable, liquid, gel, pill, tablet, and/or capsules.

In one embodiment, receipt of batches of the final product/cannabinoids 8a from vehicle 19 can each be confirmed by taggant reader 21 and delivered 20 to one or more packaging facilities, commercial or government facility, storage facilities, wholesalers, or retailers 22. When the retailer 22 distributes or sells 23 the product 8a to one or more buyers or consumers 25, the original taggants 3 can be identified and confirmed with taggant reader 24, and the product is delivered to the buyer 25. Further, the final product 8a that is in the possession of the buyer 25 can further be identified by a taggants reader and back tracked through the chain of custody to either one or more of the retailer, wholesaler, distributer, packager, processor, harvester, grower, planter, plants 8, and the original seeds 1.

Still referring to FIG. 2, in another additional embodiment of the processing/packaging stage, the plant 8 and/or product 8a may be tagged with another type of taggant 3a with bottle 6a, wherein taggant 3a is different identification data from taggant 2, and further wherein plant 4 and subsequent product 8a may now have two (2) unique identification taggants applied. In this scenario, each taggant 3a may correspond and/or identify the processor/packager facility and taggant 3 corresponding and/or identifying the grower/harvester, both being on or within the end product 8a. Here, the tagging of the plant or oil or cannabinoid end product with two or more taggants helps to further increase the security of the CCC system wherein each party or facility within the chain of custody can be identified. It is contemplated within the scope of the disclosure described herein that the grower's taggant 3 originally sprayed on the plants and the newly applied processor's unique taggant 3a will pass through the processors extraction equipment, and the unique taggant codes pair 3 and 3a being identified via one or more taggant readers.

It is contemplated within the scope of the disclosure described herein that taggants, whether the same as the seed taggants or different from the seed taggants, may be applied at any stage of the *cannabis* life cycle, such as the seed, growing, plant maturing, plant harvesting, processing, packaging, distribution, wholesale, merchant, retailer, storage, and quality control (shipping and receiving) cycle, phase, or stage. In addition, it is contemplated within the scope of the disclosure described herein that any other additional RFID tags or physical tags or codes may also be used in conjunction with the taggants described herein. Also, it is contemplated within the scope of the disclosure described herein that one custodian or one single facility may perform all the aforementioned tagging processes. For example, one single custodian location may handle both the growth/harvest stage and processing stage, or all growth/harvest, processing, distribution, merchant, etc. Alternatively, one single custodian or one single party/entity may be responsible for all the scanning, reading, or confirming of the taggants at each custodian location. In addition, one custodian or one party/entity may be responsible for depositing, spraying, binding, attaching, or encapsulating taggants on the seeds, plants, or into the oils/end product.

Figure 3:
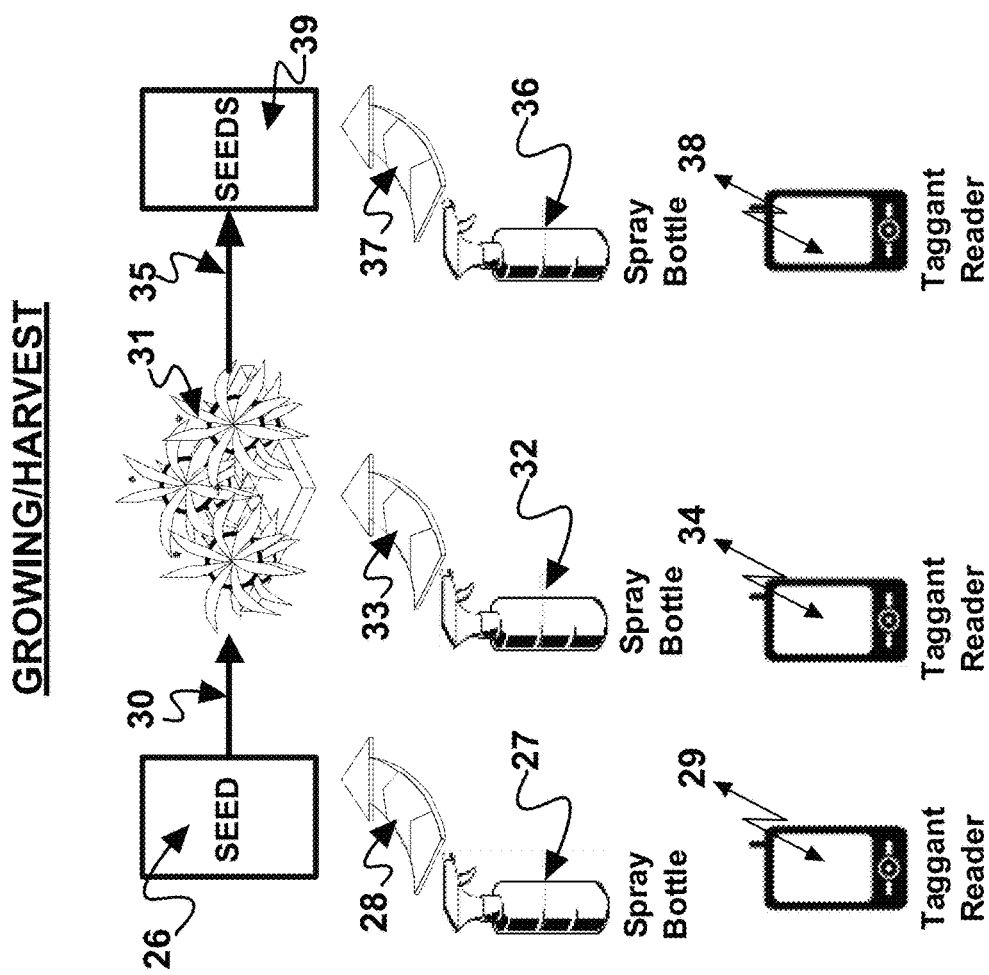
FIG. 3 illustrates a diagram for one non-limiting embodiment of the CCC system illustrating a process for tagging and reading *cannabis* seeds from a planting phase to a growth phase and to extracting additional seeds.

Referring now to FIG. 3, another embodiment of the CCC system can be shown, illustrating a grower and/or harvester seed inventory chain of custody. Here the grower is producing plants and a seed inventory as an asset, which also requires a CCC system to manage and control seed inventory and to insure that no seeds are inadvertently shipped to the processor with the harvested plants. After seeds are removed from the plants, the grown plants can then be shipped to the processor. Further, the growers CCC system also helps with managing quality control of seed production. Here, from the very first seed, many more seeds can be obtained from the grown plants to further the grower's business until a regulated growing limit is reached. It is further contemplated within the scope of the disclosure described herein that grower or harvester's tagged inventory can also be read/scanned and the data sent to a central database server.

Still referring to FIG. 3, a first starter seed package 26 can be used as a reference seed to grow plants that produce more production seeds 39 which can be recycled back to package seed 26. In this embodiment, reference package seeds 26 are tagged with taggants 28 using bottle 27 thereby tagging both the package and seeds therein with encoded identification codes. A taggants reader 29 can further confirm the sprayed taggants code 28 and the reference seed 26 can be delivered 30 to the growing area such as a green house, field, facility, or other suitable medium in order to grow *cannabis* plant 31 from seed 26. Grown or growing plant 31 can also be tagged again with either the same taggant 28 or a different taggant 33 with bottle 32. The tagging of the plants can ideally be divided into batches, each batch having unique tag codes, and wherein each batch may then be sized to accommodate the shipping packages or other means of delivery. Further, shipping/packaging labels having scanable optical bar codes, QR codes, or RFID or other codes that represent the aggregate or contents of the contained shipment, may be used to track batched shipping of the *cannabis* or end product. Here, the grown plant 31 can be segregated into manageable growth batch areas, and each batch area checked for taggant code 28 and/or taggants 33 with taggant reader 34. After plants 31 have grown or matured, the seeds can then be harvested and delivered 35 to package seeds 39. Here, package seeds 39 can then be tagged with the same taggants 28, 33, or a different taggant 37. Taggants 28, 33, and/or 37 can then be checked and confirmed by taggants reader 38 and the seeds 39 can then be placed into inventory for future use by the grower. Here, since data from taggants can be recorded and stored in a computer database, the seeds' unique taggant codes may be traced and tracked to the end user or consumer and from the end-user or consumer back to the grower inventory. This allows the grower the ability to track plant quality, potency, genetics, origin, and a processors extraction equipment performance for each batch of the end product or cannabinoid yield, including tracking the end product or oil to consumers and government authorities and reporting to government agencies.

Figure 4:
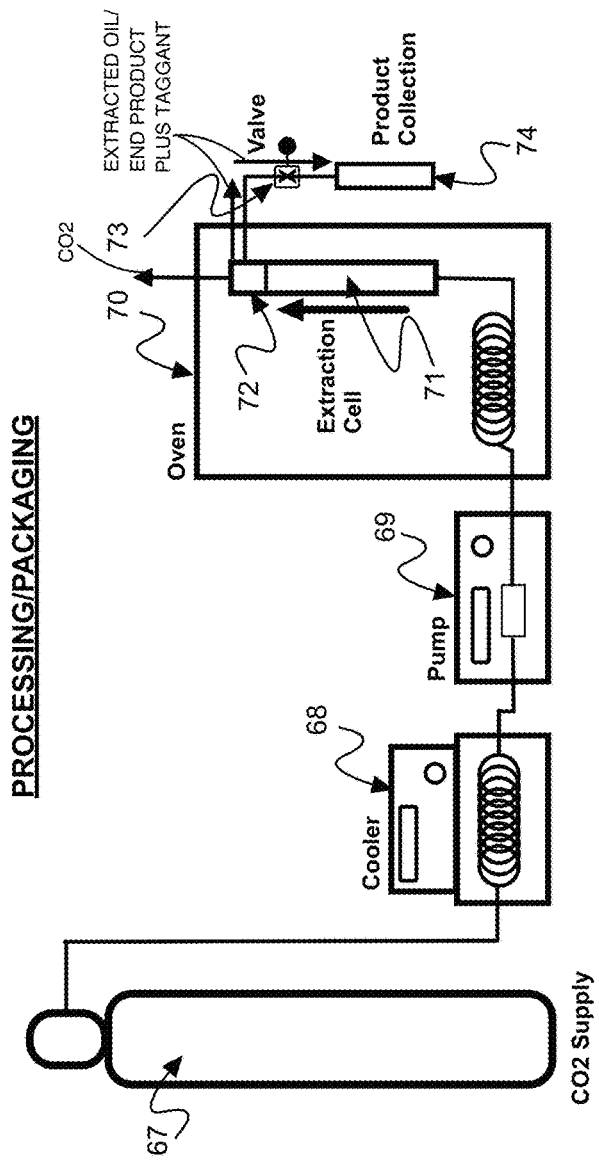
FIG. 4 illustrates components for one non-limiting embodiment of a supercritical CO2 fluid extraction system illustrating a continuous path of travel for the taggants of the CCC through the *cannabis* processing and extraction phase.

Referring now to FIG. 4, illustration of one embodiment for the processing stage of the CCC system of the disclosure described herein, namely a method of using supercritical CO2 fluid extraction or extraction equipment. Here, CO2 from a CO2 supply 67 canister is sent to a CO2 cooler 68 in communication with a high pressure pump 69 for pumping the CO2 to an oven 70. Within a chamber of 70, the CO2 enters an extraction cell 71, wherein the plant 8 material is packed. Prior to packing extraction cell 71, the plant 8 may be reduced in size by trimming the plants material and then shredded, grounded, and/or reduced to a mash or fine powder or granules. This allows for efficient and complete extraction of the oil or cannabinoid end product. The extraction cell 71 may be of a large volume and a filter 72 further coupled to the extraction cell in order to catch or remove any large debris down to very fine particles from the product oil or cannabinoid, while allowing the passage of the taggant to the product collection chamber. On one end of the extraction cell, CO2 may be released into the atmosphere while the extracted oil and included taggants travel to valve 73 and chamber 74. In addition, the released CO2 may also be recaptured or re-used. Here, valve 73 can control the filling of the final oil product or cannabinoid into a collection chamber 74, wherein the end product can be retrieved for packaging and shipping to a retailer, wholesaler, and/or distributor, among others. Here, the movement of the taggant from the surface of the plant into the extracted oil or cannabinoid through the extraction process can be characterized as the taggant transitioning from a coating of a solid state to a liquid or suspension state, wherein the taggants are dispersed, mixed, and/or are stabilized within the cannabinoid oils or extracts. More specifically, the taggant particles can be statistically distributed within the end product, oils, cannabinoids or dispersion medium. In addition, the extraction process can remove the taggant's binder thereby allowing it to be removed from the surface of the plants or seeds and allowing the taggants to be further mixed, or to be dispersed within the cannabinoids or end product as a suspension. More specifically, in one embodiment, the taggants can be a colloidal suspension within the end product or oil. It is contemplated within the scope of the disclosure described herein that the taggants cannot be separated from the seeds or plants in their natural state or in normal growth/harvesting operations, such as exposure to environmental factors like rain, humidity, moisture, wind, snow, sun, cold, heat, or exposure to pest/weed control methods or chemicals. It is contemplated within the scope of the disclosure described herein that the taggants can only be separated from the seed or plants through either the extraction process or through incorporating certain pre-defined or pre-determined methods, procedures, and/or chemicals or solvents that are specifically designed/intended to remove the taggants from the seeds or plant, or specifically intended to dissolve or remove the binder that is binding the taggants to the seeds or plant.

The shape and size of the pores or cells for filter 72 are configured such that the filter does not block the taggants within the oil or cannabinoid and allow the taggants to flow through the filter and subsequently to the product collector 74. This assures retention of all applied taggants, taggants 3, taggants 3*a*, and others in the final end product or cannabinoid, such as end product 8*a* (FIG. 2), with minimal to no loss of the taggants and maximum to complete retrieval of the taggants. Further, it is contemplated within the scope of the disclosure described herein that a different type of filter may be incorporated at another stage or later stage of the CCC system that can remove all or some of the previously applied taggants. For example, a retailer may use a certain filter for removing all or some of the taggants from the final product 8*a* prior to selling to buyers 25 (FIG. 2). Alternatively, the retailer may provide or attach a physical tag such as an RFID chip or bar code to the end product 8*a* prior to selling to buyers 25. More specifically, the retailer added tag or RFID chip or bar code must match the internal taggants, or the taggants dispersed within the end products or oils.

It is contemplated within the scope of the disclosure described herein that any other type of method for extracting oils, cannabinoids, THC, among others, may be incorporated in lieu of or in addition to the supercritical CO2 fluid extraction system, such as any solvent suitable to dissolve the oil or cannabinoids from the plants of the disclosure described herein. It is further contemplated within the scope of the disclosure described herein that any marker or taggant having readable contained coded history information may be encapsulated in a may be added to the *cannabis* plant during the extraction process by its transition from the plant to the extract oil. In addition, it is contemplated within the scope of the disclosure described herein that removal of the taggants from a part of the plant, plant leaf, or from the seed prior to the extraction process for the purpose of testing or other processes such as quality control, may be accomplished without or independent of the extraction process and production of oils or cannabinoid. The taggants removal may be performed manually, semi-automated, or by automated methods in conjunction with the prior stated solvents, abrasion or other means capable of removing the binder and the tags to a container. The tags may then be completely released from removed binder in the container by dissolving the remaining or residual binder by use of the pre-described solvent It is contemplated within the scope of the disclosure described herein that any type of taggant reader or taggant detection system can be used to detect the taggants of the disclosure described herein including but not limited to using x-ray, fluorescence analysis, various implementations of spectroscopy, electronic, photonic, magnetic, RF, chemical analysis, microcode, genetic, and other methods that are able to display the code contained within the taggant.

The embodiments set forth below represent the necessary information to enable those skilled in the art to practice the disclosure described herein and illustrate the best mode of practicing the disclosure described herein. In addition, the disclosure described herein does not require that all the advantageous features and all the advantages need to be incorporated into every embodiment of the disclosure described herein.

What is claimed is:

1. A method of managing a chain of custody for *cannabis*, comprising:
    tagging one or more *cannabis* plants at a first custodian location, wherein the tagging comprises depositing one or more identification tags having a binder onto a surface of the one or more *cannabis* plants;
    receiving the tagged *cannabis* plants at a second custodian location; and
    extracting both a cannabinoid and the identification tags from the tagged *cannabis* plants in one extraction process, wherein the extracting comprises removing the binder via supercritical extraction, thereby releasing and depositing the identification tags within the extracted cannabinoid.

2. The method of claim 1, further comprising receiving the extracted cannabinoids at a third custodian location, wherein the extracted cannabinoids includes the one or more identification tags.

3. The method of claim 2, wherein the third custodian location is comprised of a distribution or retail facility.

4. The method of claim 1, wherein the first custodian location is comprised of a seed grower or plant harvester facility.

5. The method of claim 1, wherein the second custodian location is comprised of a processing facility.

6. The method of claim 1, further comprising reading or detecting the identification tags at any of the first or second custodian locations.

7. The method of claim 6, further comprising transmitting the read identification tags to a central location.

8. The method of claim 6, wherein the reading or detecting is obtained using one or more of the following methods: photonic, magnetic, x-ray, radio frequency, chemical, microcode, florescence, genetic, electronic and spectroscopy analysis.

9. The method of claim 1, wherein the identification tags are mixed or dispersed within the extracted cannabinoid.

10. The method of claim 1, wherein the tagged one or more *cannabis* plants are comprised of *cannabis* seeds in inventory.

11. The method of claim 1, wherein the tagged one or more *cannabis* plants are comprised of matured *cannabis* plants.

12. The method of claim 1, wherein the tagged one or more *cannabis* plants are comprised of *cannabis* plant cuttings.

13. A method of managing a chain of custody for *cannabis*, comprising:
    tagging one or more *cannabis* plants at a first custodian location, wherein the tagging comprises depositing one or more identification tags having a binder onto a surface of the one or more *cannabis* plants;
    receiving the tagged *cannabis* plants at a second custodian location; and
    extracting both one or more cannabinoids and the identification tags from the tagged *cannabis* plants in one extraction process, wherein the extracting comprises removing the binder via supercritical extraction, thereby releasing and dispersing the identification tags within the one or more cannabinoids.

14. A method of managing a chain of custody for *cannabis*, comprising:
    tagging a first *cannabis* at a first custodian location, wherein the tagging comprises depositing one or more first identification tags having a binder onto a surface of the first *cannabis;*
    receiving the tagged first *cannabis* at a second custodian location; and
    extracting one or more cannabinoids and the first identification tags from the tagged first *cannabis* in one extraction process, wherein the extracting comprises removing the binder via supercritical extraction, thereby releasing and dispersing the first identification tags within the extracted one or more cannabinoids.

* * * * *